(12) United States Patent
Maier

(10) Patent No.: US 8,646,604 B2
(45) Date of Patent: Feb. 11, 2014

(54) MICRO- AND/OR NANO-STRUCTURED PACKAGING MATERIAL

(75) Inventor: Stephen Maier, Leverkusen (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 465 days.

(21) Appl. No.: 12/865,442

(22) PCT Filed: Jan. 13, 2009

(86) PCT No.: PCT/EP2009/000125
§ 371 (c)(1),
(2), (4) Date: Jul. 30, 2010

(87) PCT Pub. No.: WO2009/095151
PCT Pub. Date: Aug. 6, 2009

(65) Prior Publication Data
US 2010/0320111 A1  Dec. 23, 2010

(30) Foreign Application Priority Data
Jan. 30, 2008 (DE) .................. 10 2008 006 788

(51) Int. Cl.
*A61B 19/02* (2006.01)
(52) U.S. Cl.
USPC ........... 206/438; 206/524.1; 53/461; 428/156
(58) Field of Classification Search
USPC ........... 206/438, 439, 440, 441, 524.1, 524.2, 206/524.3, 524.9, 524.6; 53/403, 450, 461; 428/156
See application file for complete search history.

(56) References Cited

U.S. PATENT DOCUMENTS

| | | | |
|---|---|---|---|
| 3,405,027 A | 10/1968 | Wyckoff | |
| 4,331,725 A | 5/1982 | Akao | |
| 5,413,567 A | 5/1995 | Barth et al. | |
| 5,613,958 A * | 3/1997 | Kochinke et al. | 604/307 |
| 2003/0129343 A1* | 7/2003 | Galkiewicz et al. | 428/40.1 |
| 2005/0074573 A1* | 4/2005 | Bowen et al. | 428/40.1 |
| 2007/0166501 A1* | 7/2007 | Seitz et al. | 428/41.8 |
| 2007/0292650 A1* | 12/2007 | Suzuki | 428/41.8 |
| 2008/0078500 A1 | 4/2008 | Sher et al. | |
| 2008/0299347 A1* | 12/2008 | Ukei et al. | 428/41.8 |
| 2009/0254041 A1* | 10/2009 | Krag et al. | 604/180 |
| 2009/0299274 A1* | 12/2009 | Laurent et al. | 604/47 |
| 2010/0158991 A1* | 6/2010 | Okada et al. | 424/448 |
| 2010/0324507 A1* | 12/2010 | Maier | 604/289 |

FOREIGN PATENT DOCUMENTS

| | | |
|---|---|---|
| DE | 1761403 | 7/1971 |
| DE | 3806444 | 8/1989 |
| DE | 10056234 | 5/2002 |
| EP | 2003178 | 12/2008 |

* cited by examiner

*Primary Examiner* — Jacob K Ackun
(74) *Attorney, Agent, or Firm* — Frommer Lawrence & Haug LLP

(57) ABSTRACT

The invention relates to a web-form packaging material which comprises at least one layer, comprising a packaging material surface, of a sealable material, to a packaging unit with a transdermal therapeutic system and with a packaging material of this kind, and also to a process for producing a packaging unit. For this purpose, at least the abovementioned surface of the packaging material has a multiplicity of recesses and/or a multiplicity of non-recessed regions. The distance between two adjacent recesses and/or the distance between two adjacent non-recessed regions is less than five times the packaging material thickness. Moreover, the depth of the recesses is not less than 1.2 nanometers and not more than 95% of the packaging material thickness.

Figure 1:
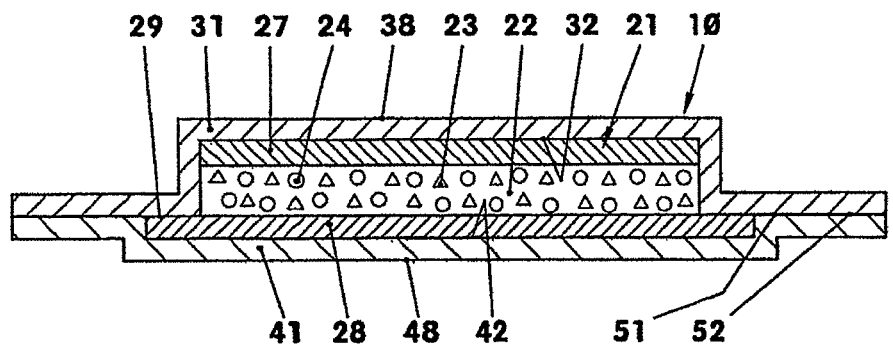

With the present invention, the sticking of an adhesive on the inner face of the packaging material is effectively prevented.

14 Claims, 3 Drawing Sheets

MICRO- AND/OR NANO-STRUCTURED PACKAGING MATERIAL

The invention relates to a web-form packaging material which comprises at least one layer, comprising a packaging material surface, of a sealable material, to a packaging unit with a transdermal therapeutic system and with a packaging material of this kind, and also to a process for producing a packaging unit.

Transdermal therapeutic systems generally possess pressure-sensitive adhesive layers or pressure-sensitive active ingredient and adhesive layers for the purpose of attaching the system to the skin of the patient. During storage and prior to application to the skin, these layers are lined on the adhesive side with a removable protective film. However, this is unable to prevent, or prevent completely, the possibility of small amounts of the adhesive material emerging in the course of storage, as a result of the "cold flow"—and to an increased degree at slightly elevated temperatures—particularly at the side marginal regions. Such emergences may result in the transdermal therapeutic systems sticking to the inside of their surrounding packaging, which has the effect, in turn, of hindering the operation of removing them from the packaging, and which may lead to a transdermal therapeutic system being destroyed. This entails avoidable costs. Moreover, the acceptance of this drug form among users is adversely affected. With storage in packaging units, therefore, there is the risk that adhesive emerging from the adhesive-containing layer will stick on the packaging material of the packaging unit, making it more difficult to remove the transdermal therapeutic system from the packaging unit.

In order to prevent sticking of the transdermal therapeutic system on the inside of the packaging, it is possible, for example, to use punching to introduce a pattern of pimples, as spacers with respect to the upper inside of the packaging material, into the edge of a protective film that juts out beyond the adhesive-containing layer. Since the products are usually conveyed using clamping jaws, the pattern of pimples may be deformed and so become useless as a spacer. This method, then, hardly prevents sticking of the transdermal therapeutic system to the inner face of the packaging material.

Furthermore, in addition to a protruding, silicone-coated or fluoropolymer-coated protective film adhering to the adhesive-containing layer, it is possible to apply a protruding, silicone-coated or fluoropolymer-coated outer film to a backing film of the transdermal therapeutic system, in order to prevent sticking of adhesive emerging at the patch edge on the inner face of the packaging material, facing the backing film. This necessitates technically costly and inconvenient incorporation of the outer film into the production operation, and the outer film must be taken into account when the transdermal therapeutic system is formulated. Moreover, when the transdermal therapeutic system is used, the outer film additionally must be disposed of.

A number of transdermal therapeutic systems or active ingredient patches have special sensitivity, on account of their composition or ingredients, and exhibit a tendency to stick on the packaging material.

The problem on which the present invention is based, therefore, is that of effectively preventing the sticking of an adhesive on the inner face of the packaging material.

This problem is solved by the features of the main claim. For this purpose, at least the abovementioned surface of the packaging material has a multiplicity of recesses and/or a multiplicity of non-recessed regions. The distance between two adjacent recesses and/or the distance between two adjacent non-recessed regions is less than five times the packaging material thickness. Furthermore, the depth of the recesses is not less than 1.2 nanometers and not more than 95% of the packaging material thickness.

In the production of the packaging unit, at least one surface of a packaging material is provided with a multiplicity of recesses and/or is provided with recesses which surround a multiplicity of non-recessed regions. The recesses are produced such that the distance between two adjacent recesses and/or the distance between two adjacent non-recessed regions is less than five times the packaging material thickness, and the depth of the recesses is not less than 1.2 nanometers and not more than 95% of the packaging material thickness. This surface of the packaging material is placed onto the side of the transdermal therapeutic system that faces away from the adhesive-containing layer. This first packaging material is joined by heat sealing to a second packaging material which is arranged on the side of the transdermal therapeutic system that faces the adhesive-containing layer. In this joining operation, a moisture-proof, gas-proof, and aroma-proof join is produced.

Further details of the invention will become apparent from the dependent claims and from the description, given below, of embodiments which are shown schematically.

Figure 2:
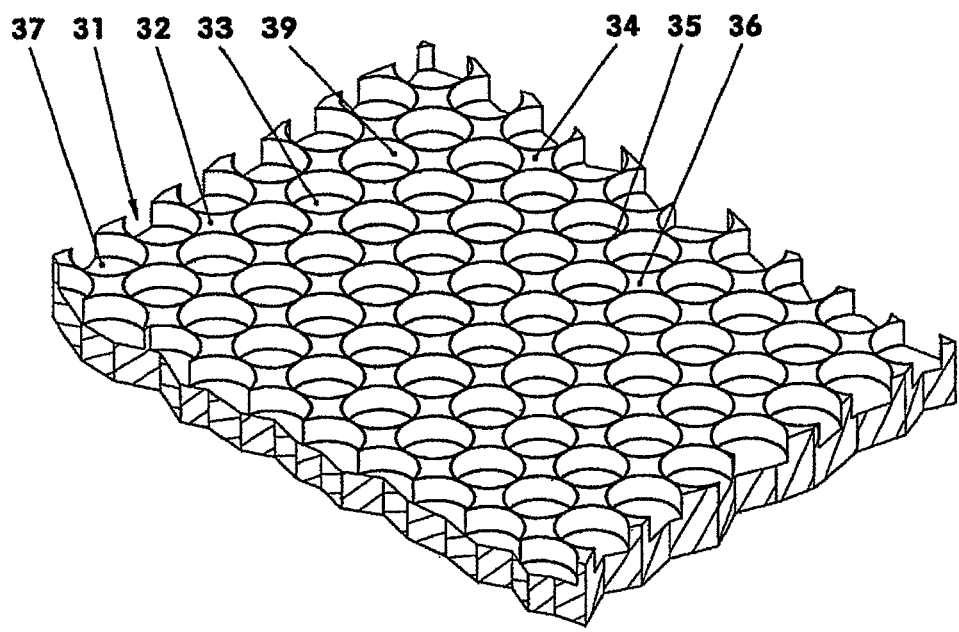
Figure 3:
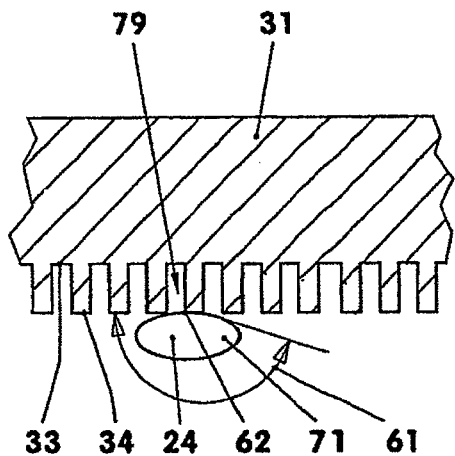
Figure 4:
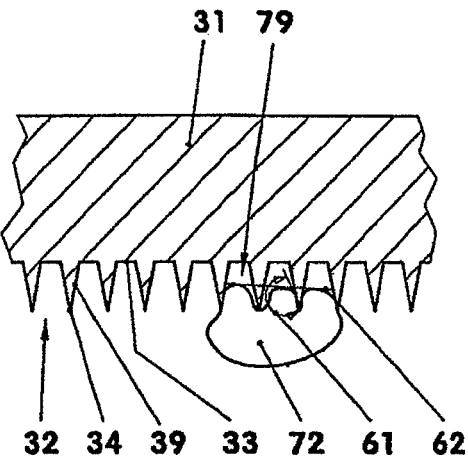
Figure 5:
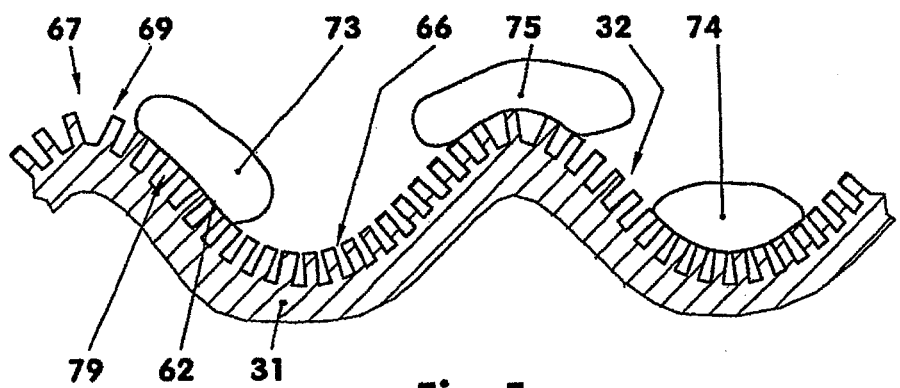
Figure 6:
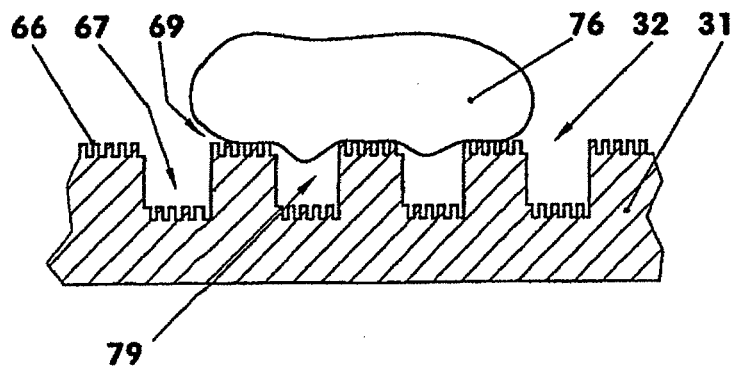
Figure 7:
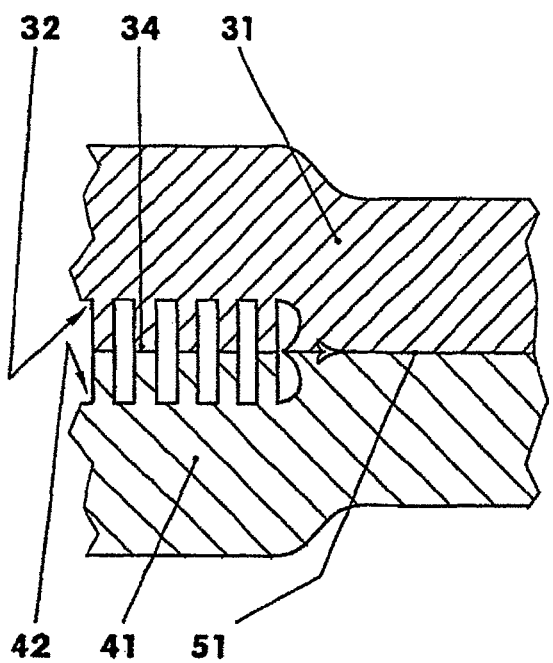
Figure 8:
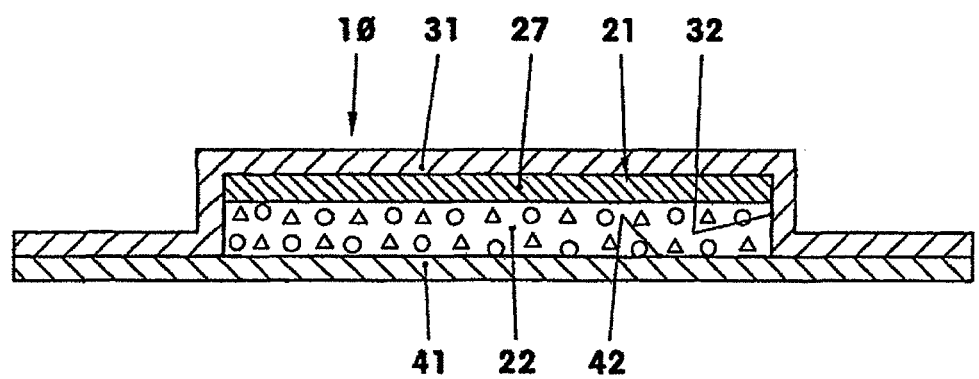

FIG. 1: Packaging unit with transdermal therapeutic system;
FIG. 2: Detail of a packaging material;
FIG. 3: Detail of a drop of adhesive on a packaging material;
FIG. 4: Pointed structures of the packaging material;
FIG. 5: Micro- and nano-structured packaging material;
FIG. 6: Variant of a micro- and nano-structured packaging material;
FIG. 7: Detail of a join seam;
FIG. 8: Packaging unit with transdermal therapeutic system without protective film.

FIG. 1 shows a packaging unit (10) with a transdermal therapeutic system (21). The packaging unit (10) comprises two packaging materials (31, 41), which enclose the transdermal therapeutic system (21) in a moisture-proof, gas-proof, and aroma-proof manner.

The transdermal therapeutic system (21) is, for example, an active ingredient patch (21) having an adhesive matrix. In this exemplary embodiment, the active ingredient (23) and the adhesive (24) are arranged in a joint layer (22) on a backing film (27). The active ingredient (23) and the adhesive (24) may, however, also be arranged in separate layers, in which case at least the layer (22) facing away from the backing film (27) contains adhesive. In a plan view of the transdermal therapeutic system (21), the backing film (27) and the active ingredient and adhesive layer (22) are, for example, the same size. Located beneath the active ingredient and adhesive layer (22) in the exemplary embodiment of FIG. 1 is a protective film (28), which attaches, for example, to the active ingredient and adhesive layer (22). At the edges (29), this protective film (28) juts out beyond the active ingredient and adhesive layer (22).

The adhesive (24), which when the transdermal therapeutic system (21) is applied ensures adhesion to the skin of the patient, is pressure-sensitive, for example. Under just gentle pressure or just slightly elevated temperature, it is possible for what is called "cold flow" to develop with this adhesive (24). In that case the adhesive (24) swells beyond the actual patch contour, in other words beyond the area of the backing film (27). The adhesive (24) is composed substantially, for example, of a matrix-forming pressure-sensitive adhesive. For this purpose it is possible to make use, for example, of polyacrylates, silicones, polyisobutylenes, rubber, rubberlike synthetic homopolymers, copolymers or block polymers, butyl rubber, styrene/isoprene copolymers, polyurethanes, copolymers of ethylene, polysiloxanes, or styrene/buta-diene copolymers, individually and/or in combination. The adhesive (24), however, may also comprise additional substances, such as, for example, physiologically active substances, dyes, plasticizers, tackifiers, permeation enhancers, etc. The surface tension of the adhesive (24) with respect to its vapor phase amounts, for example, to between 30 and 50 millinewtons per meter.

The two packaging materials (31, 41) are composed, for example, of a single-layer, film-like, sealable material or of a multilayer packaging material laminate. In the case of the multilayer packaging material laminate, at least one layer comprising a packaging material surface is composed of a sealable material. The thickness of the sealable packaging material layer or of the single-layer packaging material amounts, for example, to a tenth of a millimeter, but may also be thinner. This film, in—for example—an aroma-proof, water-proof and/or oxygen-proof form, is composed, for example, of a thermoplastic material, e.g., of polyester, polyethylene, polypropylene, polyamide, acrylonitrile-methyl acrylate copolymers, ethylene-vinyl acetate copolymers, ethylene copolymers, ionomers, etc., or mixtures thereof.

Sealing—both hot sealing and cold sealing—produces a virtually homogeneous connection between the sealing layers of the top and bottom sealing laminate. For hot sealing, use is made of heat-sealing dispersions, heat-sealing varnishes, hot-melt adhesives, and also films of thermoplastic elastomers and extrusion coatings. Cold sealing takes place, for example, using moisture, solvents, or other contact assistants, e.g., cold-sealing compositions.

In order to bring about the required proof against losses of in some cases volatile active ingredients or other ingredients, the customary packaging materials used for the packaging of transdermal therapeutic systems are furnished additionally with a barrier layer, a blocking layer. Generally speaking, this is the layer immediately to the inside of the sealing layer. The barrier layer may be composed, for example, of a continuous metal layer, such as a layer of aluminum, for example, although in principle a diffusion-proof plastics material, polyethylene terephthalate, for example, may also be contemplated. In addition, the packaging laminates may be provided with further layers, which are generally mounted on the outside, and which may be composed, for example, of paper or polymeric films. They are used, for example, for improved printability, security against unwanted ripping (child safety), or an esthetically appealing design. The thickness of the packaging material laminates amounts, for example, to a tenth of a millimeter. It can, however, also be thicker.

The packaging materials (31, 41) have—for example—sealable surfaces (32, 42) facing one another and, in the exemplary embodiment of FIG. 1, are fused thermally by heat sealing by means, for example, of four join seams (51) surrounding the transdermal system (21). At least the inwardly directed surface (32) of the upper packaging material (31) does not have a silicone or fluoropolymer coating.

A layer of thermoplastic material which serves, for example, as a sealing medium, on the inside of the packaging material, if it has a smooth surface, has a surface tension, for example, which is equal to the surface tension of the. adhesive (24) employed or has a value which differs therefrom by not more, for example, than 20%. The adhesive (24) and a smooth surface of the sealing medium therefore have a strong tendency to bond to one another. This adhesive bonding produces a firm connection which can be parted only with substantial exertion of force, as for example with a specific force of more than 5 newtons per 25 millimeters of packaging material width. In contrast, attachment means that packaging material (31; 41) and transdermal therapeutic system (21) can be parted from one another without residue, by hand, with a low expenditure of force, at a level, for example, less than the aforementioned force value.

The surface (32) of the upper packaging material (31) that is directed inwardly in FIG. 1 has recesses (33) and non-recessed regions (34). One example of a structure of this kind is shown by FIG. 2. The structure, depicted here as an extract, has cylindrical recesses (33) which are surrounded by a lattice-like non-recessed region (34). The depth of the recesses (33) is, for example, 100 nanometers. It may be between 1.2 nanometers and 95% of the packaging material thickness. The diameter of the recesses (33) shown here is, for example, 50 nanometers. It may, for example, be up to five times the packaging material thickness.

The lattice rods (35) of the non-recessed regions (34) have in this case, for example, a thickness of not more than 50 nanometers, and so, in this exemplary embodiment, two adjacent recesses (33) have a distance of 50 nanometers. This distance can be up to five times the packaging material thickness. The end face (36) is, for example, a planar face.

In the exemplary embodiment, the multiplicity of recesses (33) and of the non-recessed regions (34) is arranged regularly. The structure, however, may also be arranged irregularly; the depths of the recesses (33) may be different. The base areas (37) may be planar, concave, convex, etc., in form.

In the case of a structure having a multiplicity of non-recessed regions (34), these regions, for example, may be formed as rods having a square, round, rectangular, triangular, etc., cross section. The end faces (36) may then be of planar or convex form. The non-recessed regions (34) may be conical or pyramidal, mushroom-shaped, etc., in form.

In the case of contact of the inner face of the packaging material with an adhesive, such contact being brought about, for example, by cold flow, the structuring of the surface (32) produces a resultant active surface, in contact with the adhesive, whose properties are different from the properties of the base material. For example, with respect to an applied drop of adhesive, a surface (32) structured accordingly has a significantly lower surface energy than the smooth base material. As a result of this it is possible, for example, for adhesive bonds to develop only to a slight degree between the adhesive (24) and the inside of the packaging material. Sticking of the packaging material (31) to the transdermal therapeutic system (21) is therefore effectively prevented.

The packaging material (41) which is at the bottom in FIG. 1 may have an inwardly directed smooth surface (42). The inner surface (42) of the lower packaging material (41) may, however, also have a structure like that described in connection with the inner surface (32) of the upper packaging material (31). Where the packaging unit is configured as a triple-edged sealed pouch, the lower packaging material (41) may be part of the upper packaging material (31).

The external surfaces (38, 48) of the packaging materials (31, 41) may be smooth or structured.

The packaging unit (10) with the transdermal therapeutic system (21) is produced, for example, in a multi-stage, inter-linked operation. For example, first the active ingredient and adhesive-containing layer (22) is coated onto the backing film (27). In this case, for example, the backing film (27) is the transport film which is used to convey the semi-finished product through the production apparatus. After the drying or cooling of the active ingredient and adhesive-containing layer (22), it is covered over its full area with the protective film (28). As an alternative to this it is also possible, in the first step, to coat the protective film (28) with the active ingredient and adhesive-containing layer (22). After the drying or cooling of the active ingredient and adhesive-containing layer (22), the latter is then covered over its full area by means of the backing film (27). The laminate prepared in this way is then cut in the longitudinal direction, and subsequently passed onto a punching and packaging station.

In the punching and packaging station, the individual transdermal therapeutic system (21) is punched from the web-form laminate and then alternatively placed with the protective film (28), for example, onto the inner surface (42) of a lower packaging material web, covered with the upper packaging material web, and sealed all round, or else dispensed directly between an upper and a lower packaging material web, and sealed all round. The packaging material webs are each unwound from a roll and are conveyed, for example, continuously by means of a clamping-jaw or pincer advance system.

On the upper packaging material web, prior to use, the inner surface (32) is prepared. This may even take place outside the packaging station. The base structure that is to be applied can be generated, for example, by a holographic recording method. This is implemented, for example, by the technology of two-beam interference on the basis of coherent optical systems or of electron beam systems. In this case, for example, a glass plate coated with photoresist is introduced into an interference pattern generated by laser beams. As a result of the exposure, a pattern is produced on the resist, the spacings in said pattern being situated, for example, in the nanometer range. Using the glass plates which have been made conductive by metallization, it is possible, for example, by electro-forming or by galvanic replication, using nickel deposition, to produce copies of the structured surface. These copies can be produced in the form of plates or thin nickel sheets. The forms can then be transferred to the inside of the packaging material film by means of injection molding, thermoplastic impression, or by means of rolling. For example, the structure is applied over the entire area to the—for example—sealable surface of the packaging material web.

The web-form upper packaging material (31) prepared in this way is placed, for example, onto the web-form lower packaging material (41) and the transdermal therapeutic system (21) in such a way that the structured inner surface (32) faces the transdermal therapeutic system (21). Subsequently, the lower (41) and the upper (31) packaging materials are sealed with one another, for example, at all four edges (52), by means of heat sealing, for example.

In heat sealing, the two chemically identical but structurally, for example, different surfaces (32, 42) are joined to one another with heating. In this case, in the region of the heat-sealing seams (51), the structuring of the inner surface (32) of the upper packaging material (31) is melted, thus producing an aroma-proof, gas-proof and moisture-proof join. In FIG. 7, this is shown for an exemplary embodiment whose upper (31) and lower (41) packaging materials each have structured surfaces (32, 42) facing one another.

After the sealing operation, for example, the web-form packaging materials (31, 41) are severed. This produces packaging units (10) which each comprise, for example, one transdermal therapeutic system (21).

In the course of transit or in the course of storage it is possible that the packaging units (10) may suffer pressure loading or be exposed to slightly elevated temperatures. As a result of this it is possible for the adhesive (24) to emerge from the matrix at the sides beyond the edge of the backing film (27). In the exemplary embodiment of FIG. 1, sticking to the lower inner face (42) of the packaging material is prevented by the jutting-out edges (29) of the protective film (28). On the upper packaging material (31), the adhesive (24) conforms to the non-recessed regions (34); cf. the sectional representation in FIG. 3. In view of the small area of contact—which, in this exemplary embodiment, corresponds in each case to a section of the end face (36) of a non-recessed region (34)—the adhesive (24) wets the inside of the packaging material (32) hardly at all, and contracts to form, for example, a drop or lens shape. For example, between the drop (71) of adhesive shown in FIG. 3 and the packaging material (31), a contact angle (61) of 160 degrees is formed. In this case, the drop (71) of adhesive behaves exactly like a layer of adhesive which is applied, for example, two-dimensionally to the structured surface (32) of the packaging material (31). The drop (71) of adhesive lies only loosely on the upper packaging material (31) or attaches gently to it. When the patch (21) is removed from the packaging unit (10), it is removed without residue.

On the basis of the structuring of the surface (32), the physical properties, for example, of the bond between the packaging material (31) and the adhesive (24) are influenced. For instance, as compared with full-area application of adhesive, the effective surface that results is significantly reduced, and hence, also, the effective surface energy of the packaging material surface (32) is reduced as compared with the unstructured material. This produces only a weak adhesive bond between the packaging material (31) and the adhesive (24). Adhesive bonding of the two materials is prevented.

FIG. 4 shows a drop (72) of adhesive which extends over a plurality of non-recessed regions (34)—which in this case, by way of example, have a pyramidal form. In regions, it has penetrated into the recesses (33).

Above the drop (72) of adhesive, in the recesses (33), an air cushion (79) has formed, which prevents further penetration of the recess (33) by the drop (72) of adhesive. The depth of the recess (33) above the drop (72) of adhesive is greater than the range of the chemical and of the physical forces of adhesion between the materials. The range of the last-mentioned forces is, for example, between 0.2 nanometer and one nanometer. The depth of the recesses (33) is at least 1.2 nanometers.

On this effective surface (62) composed of air cushions (79) and non-recessed regions (34)—such surfaces are referred to, for example, as composite surfaces—the drop (72) of adhesive sits with just a little adhesion.

For example, in the recesses (33), it forms a contact angle of, for example, 160 degrees with the flanks (39) of the non-recessed regions (34).

FIG. 5 shows a packaging material (31) having a microstructure (67) and having a nanostructure (66), on which there are a number of drops (73-75) of adhesive. In the section shown, the microstructure (67) has, for example, the form of a sinusoidal curve. The distance between the individual maxima (69)—which is, for example, between one micrometer and five times the thickness of the packaging material—is sufficiently large, in this exemplary embodiment, to allow the drops (73-75) of adhesive to follow the contour. Along the microstructure (67) a nanostructure (66) is introduced into the packaging material. The distance between the individual recesses (33) of the nanostructure (66) is, for example, less than one micrometer. The construction of the latter is, for example, of the kind described in connection with FIGS. 1 to 3. The packaging material may also be provided only with a microstructure (67) or only with a nanostructure (66).

The composite surface with the air cushions (79) in the recesses (33) prevents excessive attachment and sticking of the drops (72, 73, 74) of adhesive on the packaging material (31).

FIG. 6 shows a packaging material (31) having a microstructure (67) and a nanostructure (66), where the wavelength of the microstructure (67) is shorter in form than in the representation of FIG. 5. The drop (76) of adhesive does not follow the contour of the microstructure (67), but instead lies only on its maxima (69). If in spite of this, as a result, for example, of temperature or pressure effects, a drop (76) of adhesive were to follow the contour of the microstructure (67), the overlaid nanostructure (66) would prevent sticking of the drop (76).

FIG. 8 shows a packaging unit (10) where the transdermal therapeutic system (21) is implemented without a protective film (28). For the production of this embodiment, for example, the structured lower packaging material web (41) can be coated like a protective film directly with the active ingredient and adhesive-containing layer (22), or else a backing film (27) is coated with the active ingredient and adhesive-containing layer (22). After drying and/or cooling, this layer (22) is covered directly with the structured lower packaging material web (41). The lower packaging material web (41) in this embodiment also takes on all of the functions of a protective film, both during production and in the completed packaging unit. In this exemplary embodiment, the surfaces (32, 42) of the lower packaging material (41) and of the upper packaging material (31), said surfaces facing the transdermal therapeutic system (21), are structured, as shown in FIG. 2, for example. Alternatively the configuration of the two mutually facing surfaces (32, 42) may be as shown in FIGS. 4-6. On heat sealing, the microstructures (67) and/or nanostructures (66) of the two packaging materials (31, 41) are dissolved in the region of connection; cf. FIG. 7. When the transdermal therapeutic system (21) is withdrawn from the packaging unit (10), therefore, it is firmly bonded neither to the lower (41) nor to the upper (31) packaging material. It merely attaches weakly to the lower and/or upper packaging material inner face, and can be removed easily and without residue.

Furthermore, the microstructure and/or nanostructure described for the packaging materials (31, 41) does not impair the visual impression presented by the packaging unit (10), as in the case, for example, of an embodiment of the packaging unit (10) with transparent packaging materials (31, 41).

Combinations of the exemplary embodiments described are also conceivable.

LIST OF REFERENCE NUMERALS 10 packaging unit
21 transdermal therapeutic system, patch
22 adhesive-containing layer, active ingredient and adhesive layer
23 active ingredient
24 adhesive
27 backing film
28 protective film
29 edges
31 upper packaging material, first packaging material
32 inner surface of (31), packaging material surface
33 recesses
34 non-recessed regions
35 lattice rods
36 end faces
37 base areas
38 external surface
39 flanks
41 lower packaging material, second packaging material
42 inner surface of (41)
48 external surface
51 join seams, heat-seal seams
52 edges
61 contact angle
62 effective surface
66 nanostructure
67 microstructure
69 maxima of (67)
71-76 drops of adhesive
79 air cushion

The invention claimed is:

1. A web-form packaging material comprising:
at least one layer, comprising packaging material surface, of a sealable material;
wherein the packaging material surface has:
a multiplicity of recesses; and
multiplicity of non-recessed regions;
wherein a maximum distance between two adjacent recesses and a maximum distance between two adjacent non-recessed regions are each less than five times a thickness of the packaging material; and
wherein a depth of the recesses is not less than 1.2 nanometers and not more than 95% of the packaging material thickness.

2. The packaging material of claim 1;
wherein a structuring marked by the recesses is made over the full area in this packaging material surface.

3. The packaging material of claim 1;
wherein the thickness of the packaging material is 0.1 mm or less.

4. The packaging material of claim 1;
wherein the packaging material comprises a material selected from the groups consisting of polyamide, acrylonitrile-methyl acrylate copolymers, ethylene-vinyl acetate copolymers, ethylene copolymers, ionomers, and mixtures thereof.

5. A packaging unit with comprising:
a first packaging material;
a second packaging which is sealed to the first packaging material in an aroma-proof, gas-proof, and moisture-proof manner; and
a transdermal therapeutic system which comprises an adhesive layer, and which is arranged between the first packaging material and the second packaging material,
wherein:
the first packaging material comprises the packaging material of claim 1; and
the second packaging material comprises at least one layer, comprising a packaging material surface, of a sealable material;
wherein the first and second packaging materials are sealed to each other so that the packaging, material surfaces of the first and second packaging materials, respectively, face each other.

6. The packaging unit of claim 5;
wherein the adhesive is pressure-sensitive.

7. The packaging unit of claim 5;
wherein the transdermal therapeutic system has a protective film which juts out on all sides.

8. The packaging unit of claim 5;
wherein each of the first and second packaging materials comprises the packaging material of claim 1.

9. The packaging unit of claim 5;
wherein the second packaging material is part of the first packaging material.

10. The packaging unit of claim 6;
wherein the transdermal therapeutic system has a protective film which juts out on all sides.

11. The packaging unit of claim 10;
wherein each of the first and second packaging materials comprises the packaging material of claim 1.

12. The packaging unit of claim 11;
wherein the second packaging material is part of the first packaging material.

13. The packaging unit of claim 5;
wherein the transdermal therapeutic system further comprises a backing film; and
wherein the transdermal therapeutic system is arranged between the first and second packaging materials so that the film is located between the first packaging material and the adhesive layer.

14. A process for producing a packaging unit with a transdermal therapeutic system comprising an adhesive-containing layer, comprising:

providing at least one surface of a first packaging material with a multiplicity of recesses and a multiplicity of non-recessed regions;
wherein the recesses are produced such that:
at least one of a distance between two adjacent recesses and a distance between two adjacent non-recessed regions is less than five times the packaging material thickness; and
a depth of the recesses is not less than 1.2 nanometers and not more than 95% of the packaging material thickness;
wherein the at least one surface of the first packaging material is placed onto a side of the transdermal therapeutic system that faces away from the adhesive-containing layer; and
wherein the first packaging material is joined to a second packaging material, which is arranged on a side of the transdermal therapeutic system that faces the active ingredient and adhesive layer, by means of sealing, to produce join seams which are moisture-proof, gas-proof, and aroma proof.

* * * * *

UNITED STATES PATENT AND TRADEMARK OFFICE
CERTIFICATE OF CORRECTION

| | | |
|---|---|---|
| PATENT NO. | : 8,646,604 B2 | Page 1 of 1 |
| APPLICATION NO. | : 12/865442 | |
| DATED | : February 11, 2014 | |
| INVENTOR(S) | : Stephan Maier | |

It is certified that error appears in the above-identified patent and that said Letters Patent is hereby corrected as shown below:

The following should be deleted from the title page of the patent after item (75):

"Inventor:   Stephen Maier, Leverkusen (DE)"

The following should be inserted on the title page after item (75):

--Inventor:   Stephan Maier, Leverkusen (DE)--

Signed and Sealed this
Twenty-ninth Day of April, 2014

Michelle K. Lee
*Deputy Director of the United States Patent and Trademark Office*